US012728096B2

(12) United States Patent
Fradera Gelabert et al.

(10) Patent No.: US 12,728,096 B2
(45) Date of Patent: Sep. 8, 2026

(54) PHARMACEUTICAL COMPOSITION COMPRISING ENZALUTAMIDE

(71) Applicant: Synthon B.V., Nijmegen (NL)

(72) Inventors: Sara Fradera Gelabert, Sant Boi de Llobregat (ES); Lisardo Alvarez Fernandez, Sant Boi de Llobregat (ES); Rohit Kumar, Sant Boi de Llobregat (ES)

(73) Assignee: Synthon B.V., Nijmegen (NL)

( * ) Notice: Subject to any disclaimer, the term of this patent is extended or adjusted under 35 U.S.C. 154(b) by 1107 days.

(21) Appl. No.: 17/765,934

(22) PCT Filed: Oct. 1, 2020

(86) PCT No.: PCT/EP2020/077565
§ 371 (c)(1),
(2) Date: Apr. 1, 2022

(87) PCT Pub. No.: WO2021/064123
PCT Pub. Date: Apr. 8, 2021

(65) Prior Publication Data

US 2022/0347102 A1 Nov. 3, 2022

(30) Foreign Application Priority Data

Oct. 3, 2019 (EP) .................................... 19201339

(51) Int. Cl.

| | |
|---|---|
| ***A61K 9/20*** | (2006.01) |
| ***A61J 3/00*** | (2006.01) |
| ***A61J 3/10*** | (2006.01) |
| ***A61K 31/4166*** | (2006.01) |

(52) U.S. Cl.
CPC ............. *A61K 9/2054* (2013.01); *A61J 3/005* (2013.01); *A61J 3/10* (2013.01); *A61K 9/2018* (2013.01); *A61K 9/2031* (2013.01); *A61K 9/2095* (2013.01); *A61K 31/4166* (2013.01)

(58) Field of Classification Search
CPC .. A61K 9/2054; A61K 9/2018; A61K 9/2031; A61K 9/2095; A61K 31/4166; A61J 3/005; A61J 3/10
See application file for complete search history.

(56) References Cited

U.S. PATENT DOCUMENTS

2018/0148417 A1 5/2018 Suzuki et al.

FOREIGN PATENT DOCUMENTS

| | | |
|---|---|---|
| CN | 109432016 | 3/2019 |
| WO | WO2006124118 | 11/2006 |
| WO | WO2014043208 | 3/2014 |
| WO | WO2014167428 | 10/2014 |
| WO | WO2015118015 | 8/2015 |
| WO | WO2016/016665 | 2/2016 |
| WO | WO2016194813 | 6/2018 |

OTHER PUBLICATIONS

Vo et al., "Current trends and future perspectives of solid dispersions containing poorly water-soluble drugs," *Eur. J. Pharm. Biopharm.*, 85 (2013) pp. 799-813.
Tran et al., "Overview of the Manufacturing Methods of Solid Dispersion Technology for Improving the Solubility of Poorly Water-Soluble Drugs and Application to Anticancer Drugs," *Pharmaceutics*, (2019), 11,132, pp. 1-26.
Shah et al., "Improved Human Bioavailability of Vemurafenib, a Practically Insoluble Drug, Using an Amorphous Polymer-Stabilized Solid Dispersion Prepared by a Solvent-Controlled Coprecipitation Process," *Journal of Pharmaceutical Sciences*, vol. 102, No. 3, Mar. 2013, pp. 967-981.
Wilson et al., "Relationship between amorphous solid dispersion in vivo absorption and in vitro dissolution: phase behavior during dissolution, speciation, and membrane mass transport," *Journal of Controlled Release*, vol. 292, (2018), pp. 172-182.

*Primary Examiner* — George W Kosturko
*Assistant Examiner* — William Y Lee
(74) *Attorney, Agent, or Firm* — Buscher Patent PLLC

(57) ABSTRACT

The present invention relates to a tablet composition comprising a granulate consisting of a co-precipitate on a substrate, wherein the co-precipitate comprises enzalutamide in amorphous form and a cellulosic concentration enhancing polymer. The invention further relates to the use of said composition as a medicament, particularly in the treatment of castration-resistant prostate cancer.

15 Claims, 1 Drawing Sheet

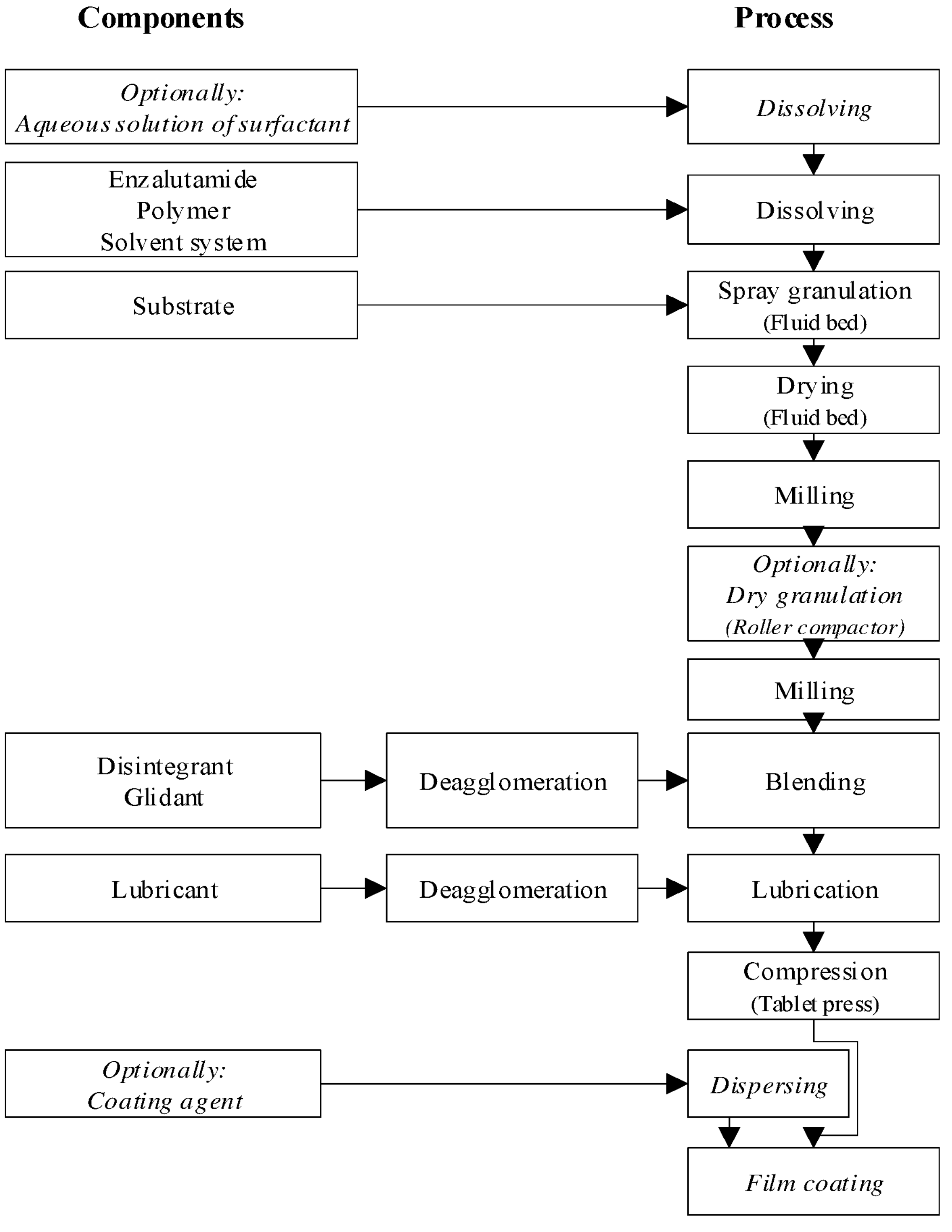
Components
Process
Optionally:
Aqueous solution of surfactant
Dissolving
Enzalutamide
Polymer
Solvent system
Dissolving
Substrate
Spray granulation
(Fluid bed)
Drying
(Fluid bed)
Milling
Optionally:
Dry granulation
(Roller compactor)
Milling
Disintegrant
Glidant
Deagglomeration
Blending
Lubricant
Deagglomeration
Lubrication
Compression
(Tablet press)
Optionally:
Coating agent
Dispersing
Film coating

PHARMACEUTICAL COMPOSITION COMPRISING ENZALUTAMIDE

BACKGROUND OF THE PRESENT INVENTION

Enzalutamide, chemically 4-[3-[4-cyano-3-(trifluoromethyl)phenyl]-5,5-dimethyl-4-oxo-2-sulfanylideneimidazolidin-1-yl]-2-fluoro-N-methylbenzamide of formula (I), (I)

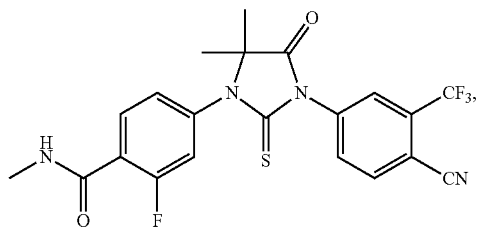

is a pharmaceutically active compound. It is used for the treatment of castration-resistant prostate cancer.

Enzalutamide is marketed by Astellas under the brand name Xtandi® and is disclosed in WO2006124118. Xtandi® was initially only supplied as immediate release liquid-filled soft gelatin capsule in one strength: 40 mg. The recommended dose is 160 mg, four 40 mg soft capsules, as single oral daily dose. The European Medicines Agency approved in July 2017 a new tablet formulation of Xtandi®. The film-coated tablet is available in two strengths: 40 and 80 mg. This tablet offers a new dosage form with reduced size compared to the capsule to help address the needs in patients having difficulty swallowing.

WO2014043208 discloses polymorphic form A of enzalutamide. A crystallization process to prepare the crystalline form A is disclosed in WO2016194813.

Enzalutamide is a BCS class II compound, exhibiting low solubility and high permeability. The Xtandi® tablet formulation comprises a spray dried dispersion of enzalutamide and hydroxypropylmethylcellulose acetate succinate (HPMCAS). The formulation is disclosed in WO2014043208.

WO2014167428 discloses solid dispersions comprising enzalutamide and at least one carrier. The carrier may be a polymer, cyclodextrin or gelatin and is used in a quantity ranging between 5-50% (w/w) with regard to enzalutamide. The solid dispersion is obtained by heating a solution of enzalutamide in the presence of the carrier, and drying the obtained mixture by e.g. distillation.

WO2015118015 discloses adsorbates and solid dispersions comprising enzalutamide and a surfactant. The polymer used for the solid dispersion is preferably selected from the group consisting of HPMC, HPC, PVP and PVA. After drying, the granulate was filled into hard gelatin capsules.

CN109432016 discloses ternary solid dispersions comprising enzalutamide, HPMCAS and a third component, selected from trehalose, maltitol, cyclodextrin and Dowfax 21A. The third component improves the solubility, dissolution and bioavailability of enzalutamide. The ternary solid dispersions are prepared by applying ultrasonic dissolution and spray drying.

In view of the prior art cited above, there is still a need for pharmaceutical tablet compositions comprising enzalutamide in amorphous form, which are suitable for production on commercial scale by applying techniques and equipment commonly used in industry in an efficient and cost-effective process and which exhibit excellent long term stability.

BRIEF DESCRIPTION OF THE PRESENT INVENTION

The present invention provides a tablet composition comprising a granulate consisting of a co-precipitate on a substrate, wherein the co-precipitate comprises enzalutamide in amorphous form and a cellulosic concentration enhancing polymer.

It also provides a process to prepare the tablet composition comprising the following steps:

a) Dissolving enzalutamide, the cellulosic concentration enhancing polymer and optionally a surfactant in a solvent system comprising acetone;
b) Spraying the solution over the substrate;
c) Drying the obtained granulate;
d) Blending with further pharmaceutically acceptable excipients;
e) Compressing into tablets;
f) Optionally coating of the tablets.

Said pharmaceutical composition may be used as a medicament, particularly in the treatment of castration-resistant prostate cancer.

BRIEF DESCRIPTION OF THE DRAWINGS

FIG. 1 shows the flow chart of the process applied to prepare the tablets of Examples 1-4.

DETAILED DESCRIPTION OF THE PRESENT INVENTION

The film-coated tablet Xtandi® offers, in addition to the liquid-filled soft gelatin capsule, a new dosage form having reduced size to help address the needs in patients having difficulty swallowing.

Enzalutamide is practically insoluble in water at pH 1 to 11. Various approaches to overcome the poor aqueous solubility of drug candidates have been investigated in drug research and development. Since the solubility of amorphous forms is higher compared to the solubility of crystalline forms, it is desirable to have enzalutamide available in amorphous form. However, drugs that can exist in either amorphous or crystalline form tend to crystallize over time when present in amorphous state because the crystalline form of the drug is a lower-energy state than the amorphous form.

One of the most successful and potent strategies to improve the dissolution of poorly soluble drugs is the preparation of a solid dispersion. The term solid dispersion has been defined as a dispersion of one or more Active Pharmaceutical Ingredients (APIs) in an inert carrier or matrix at the solid state, prepared by a solvent or melting process or a combination of the two. A kneading method may also be applied to obtain a solid dispersion. Depending on the physical state of the carrier, which is crystalline or amorphous, the solid dispersions are divided into crystalline solid dispersions and amorphous solid dispersions respectively. Amorphous carriers used are mostly polymers. In amorphous solid dispersions, the API is dispersed in very small size and exists in supersaturated state in amorphous carriers because of forced solubilization. The amorphous carriers can increase the wettability and dispersibility of drugs as well as inhibit the precipitation process of drugs when amorphous solid dispersions are dissolved in water. These properties along with the fast dissolution rate of amorphous carriers enhance the drug solubility and release rate.

Despite the high active research interests, the number of marketed products arising from solid dispersion approaches is still limited. This low number is mainly due to scale-up problems and physicochemical instability in the manufacturing process or during storage leading to phase separation and crystallization (Vo et al., Eur. J. Pharm. Biopharm., 85 (2013) 799-813; Tran et al., Pharmaceutics, 11 (2019), 11, 132).

It is not self-evident that a given drug will form an amorphous solid dispersion with just any polymer, and that, even in the event the solid dispersion is formed, it will be stable over time. Factors playing a role herein are the physicochemical properties of both API and polymer, the ratio of API to polymer used and the technique used to prepare the solid dispersion. Techniques to prepare solid dispersions often require very specific conditions for each combination of API and polymer.

Processes like freeze drying and spray drying are known to prepare solid dispersions. However, these techniques require specific, expensive equipment and the material obtained by applying these techniques is often difficult to handle due to its fluffy character.

In addition, solid dispersions can be prepared by the process of hot melt extrusion. This technique has the advantage of being a continuous manufacturing process that does not require the use of solvents and that yields a product with high density. However, the process of hot melt extrusion has also some serious drawbacks. Because of the high temperatures applied, problems related to decomposition frequently occur. Moreover, the process of hot melt extrusion requires specific equipment, which is not present in most pharmaceutical production plants.

The Xtandi® tablet formulation comprises a spray dried dispersion of enzalutamide and the polymer HPMCAS. As mentioned, the technique of spray drying requires specific, expensive equipment and may have as drawback that low density material is obtained, which is difficult to process further into the final drug product.

The present invention provides a tablet composition comprising a granulate consisting of a co-precipitate on a substrate, wherein the co-precipitate comprises enzalutamide in amorphous form and a cellulosic concentration enhancing polymer.

The granulate consisting of the co-precipitate on the substrate provides a substance which is surprisingly easy to process and work with. In contrast to the solid dispersion obtained by spray drying a solution of enzalutamide and the cellulosic concentration enhancing polymer, the granulate consisting of the co-precipitate on the substrate results in a solid with high density.

The granulate, obtained by spraying the solution of enzalutamide and the cellulosic concentration enhancing polymer over the substrate and subsequently drying, is in the form of a free-flowing powder with excellent handling properties. The preparation of the granulate does not require specific equipment, but can be obtained with equipment commonly used in pharmaceutical industry, like a fluid bed granulator. The tablet composition comprising the granulate is very stable and is bioequivalent to the Xtandi® film-coated tablet.

The weight ratio of enzalutamide to the cellulosic concentration enhancing polymer in the co-precipitate ranges from 1:2 to 1:6. Preferably, the weight ratio ranges from 1:3 to 1:5. Most preferably, the weight ratio ranges from 1:4 to 1:5.

In general, polymers that have been reported as being suitable for use as concentration enhancing polymers to increase the bioavailability of poor water soluble drugs are povidone (PVP), copovidone (PVPVA), crospovidone (crosPVP), polyethyleneglycols (PEG), polymethacrylates, hydroxypropylmethylcellulose (HPMC), hydroxypropylmethylcellulose acetate succinate (HPMCAS), hydroxypropylmethylcellulose phthalate (HPMCP), hydroxyethylcellulose (HEC), hydroxypropylcellulose (HPC), polyvinyl acetate phthalate (PVAP), cellulose acetate phthalate (CAP), poloxamers, carbomers and Soluplus®. Suitable concentration enhancing polymers to be used in accordance with the present invention are the cellulosic polymers. Particularly preferred polymers to be used in the tablet composition of the present invention within the group of cellulosic concentration enhancing polymers are HPMCAS and HPMCP.

HPMCAS is available in three grades, differentiated by the degree of substitution, resulting in a pH dependent dissolution: low (L), medium (M) and high (H). Each grade is available in two particle sizes: cohesive fine powder (F) and free-flowing granules (G). In principle, every grade of HPMCAS may be used in accordance with the present invention. Grades L and M are particularly preferred grades. Most preferred grade to be used in accordance with the present invention is grade MG.

HPMCP is available in three grades, differentiated by the degree of substitution, pH solubility in buffer solution and viscosity: HP-50, HP-55 and HP-55S. All grades of HPMCP may be used in accordance with the present invention. Grades HP-50 and HP-55 are particularly preferred grades. Most preferred grade to be used in accordance with the present invention is grade HP-55.

The substrate in accordance with the present invention may be water soluble or water insoluble and is preferably selected from a sugar alcohol (water soluble), microcrystalline cellulose (water insoluble) or mixtures thereof. A particularly preferred sugar alcohol to be used as substrate in accordance with the present invention is mannitol. In addition to the sugar alcohol and/or microcrystalline cellulose, the substrate may comprise a disintegrant. This may be any disintegrant known to a person skilled in the art. Most preferably, the disintegrant used in the substrate is croscarmellose sodium. The weight ratio of enzalutamide to the cellulosic concentration enhancing polymer to the substrate ranges from 1:2:0.5 to 1:6:5. Preferably, the weight ratio of enzalutamide to the cellulosic concentration enhancing polymer to the substrate ranges from 1:3:1 to 1:5:3.

The co-precipitate may, besides enzalutamide and the cellulosic concentration enhancing polymer, further comprise a surfactant. The surfactant may be added to improve the wettability of the drug particles and result in faster dissolution behavior of the tablet composition. The surfactant to be used in accordance with the present invention may be any surfactant known to a person of ordinary skill in the art, but is preferably a non-ionic surfactant. The non-ionic surfactant in accordance with the present invention may be any non-ionic surfactant known to a person skilled in the art. Suitable non-ionic surfactants are selected from the group consisting of sorbitan esters, polysorbates and poloxamers. A particularly preferred non-ionic surfactant to be used in accordance with the present invention is a poloxamer. Poloxamers are synthetic block copolymers of hydrophilic poly(oxyethylene) and hydrophobic poly(oxypropylene). Properties such as viscosity, HLB and physical state are dependent on the relative chain lengths of the hydrophilic and hydrophobic blocks. Poloxamers are supplied commercially as Pluronic®, Kolliphor®, Lutrol® and Synperonic®. Poloxamer 188, commercially available as Pluronic® F-68, Kolliphor® P 188, Lutrol® F-68 or Synperonie F68, is a particularly preferred non-ionic surfactant to be used in accordance with the present invention. The surfactant is preferably present in the tablet composition in an amount ranging from 0.5 to 3% w/w relative to the total weight of the tablet. Most preferably, the amount of surfactant in the tablet composition ranges from 1 to 2% w/w relative to the total weight of the tablet.

The tablet composition, comprising a granulate consisting of a co-precipitate on a substrate, may further comprise pharmaceutically acceptable excipients. The excipients to be used in accordance with the present invention are well-known and are those excipients which are conventionally used by the person skilled in the art in pharmaceutical compositions. The excipients are selected from one or more diluents, disintegrants, glidants or lubricants.

The diluent to be used in accordance with the present invention may be any diluent known to a person of ordinary skill in the art. Particularly, the diluent to be used in accordance with the present invention is an inorganic diluent, polysaccharide, mono- or disaccharide or sugar alcohol. Microcrystalline cellulose is a particularly preferred diluent.

The disintegrant to be used in accordance with the present invention may be any disintegrant known to a person of ordinary skill in the art. Suitable disintegrants to be used in accordance with the present invention are selected from the group consisting of croscarmellose sodium, crospovidone or sodium starch glycolate. Croscarmellose sodium is a particularly preferred disintegrant.

The glidant to be used in accordance with the present invention may be any glidant known to a person of ordinary skill in the art. Colloidal silicon dioxide is a particularly preferred glidant.

The lubricant to be used in accordance with the present invention may be any lubricant known to a person of ordinary skill in the art. Magnesium stearate is a particularly preferred lubricant.

The pharmaceutical composition of the present invention exhibits excellent long term stability. After storage of the composition in blisters at 40° C./75% RH, no conversion of enzalutamide into any crystalline form was observed.

The tablet composition according to the present invention displays dissolution behavior typical for immediate-release formulations. The composition of the present invention exhibits a dissolution rate of less than 15% in 30 minutes when tested in 300 ml 0.03 N hydrochloric acid pH 1.2 and at least 75% in 90 minutes when tested in 900 ml phosphate buffer pH 6.8 in a USP apparatus II at 50 rpm (normal vessel) at 37° C.

The process to prepare the tablet composition of the present invention comprises the following steps:

a) Dissolving enzalutamide, the cellulosic concentration enhancing polymer and optionally a surfactant in a solvent system comprising acetone;
b) Spraying the solution over a substrate;
c) Drying the obtained granulate;
d) Blending with further pharmaceutically acceptable excipients;
e) Compressing into tablets;
f) Optionally coating of the tablets.

Major advantage of the process to prepare the tablet composition of the present invention is that it does not require specific equipment, but that it can be executed with equipment commonly used in pharmaceutical industry, like a fluid bed granulator.

Moreover, the process to prepare the tablet composition in accordance with the present invention is very efficient. According to the information published by the EMA in the European Public Assessment Report (EPAR), the process used by Astellas to prepare Xtandi® film-coated tablets requires, after the step of spray drying the solution of enzalutamide and HPMCAS in acetone, a step of secondary drying to lower the limits of the residual acetone to acceptable levels. After the step of secondary drying, the spray drying intermediate, comprising enzalutamide and HPMCAS, is blended with intragranular excipients and a dry granulation process (slugging) is applied.

In the process whereby the tablet composition of the present invention is prepared, the steps of secondary drying and dry granulation are superfluous. The tablet composition in accordance with the present invention is prepared by a simple, robust and efficient process and does not require specific equipment. The granulate, obtained by spraying the solution of enzaluatamide and the cellulosic concentration enhancing polymer over the substrate and subsequently drying, is in the form of a free-flowing powder with excellent handling properties. The tablet composition is very stable and is bioequivalent to the Xtandi® film-coated tablet.

In the process to prepare the tablet composition in accordance with the present invention, enzalutamide and the cellulosic concentration polymer are dissolved in a solvent system comprising acetone. In addition to acetone, the solvent system may contain any other organic solvent or water, or combinations thereof. Optionally, surfactant is added to the solution comprising enzalutamide and the cellulosic concentration enhancing polymer. Preferably, the surfactant is added as an aqueous solution.

An advantage of the process of the present invention is that it requires less solvent to prepare the granulate when compared to the amount of solvent used to prepare a spray-dried dispersion of enzalutamide and a cellulosic concentration enhancing polymer.

The solution comprising enzalutamide and the polymer, and optionally the surfactant, is then sprayed over a substrate. This is executed with equipment commonly used in the pharmaceutical industry. Preferably a fluid bed granulator is used.

The obtained granulate is then dried. Preferably, the drying is performed in the same equipment as wherein the granulate is prepared. Most preferably, the drying is executed in a fluid bed granulator.

The process to prepare the tablet composition of the present invention may comprise optionally, after drying the granulate, the extra step of dry granulation in order to increase the density of the granulate further.

The granulate, comprising enzalutamide and the cellulosic concentration enhancing polymer, is blended with further excipients.

The blend with further excipients is compressed into tablets, which may optionally be coated by a film-coat. The coating serves generally cosmetic purposes. The coating material typically has no influence on the release rate, except of an inherent short initial delay in dissolution due to the time necessary to dissolve the coating. The coating may be selected from amongst one or more of those suitable coating materials known in the art.

The coating may be performed by applying one or more film forming polymers, with or without other pharmaceutically inert excipients, as a solution/suspension. Coating is done using any conventional coating technique known in the art, such as spray coating in a conventional coating pan or fluidized bed processor; or dip coating.

The pharmaceutical composition of the present invention exhibits excellent long term stability. After storage of the composition in blisters at 40° C./75% RH, no conversion of enzalutamide into any crystalline form was observed.

The tablet composition according to the present invention displays dissolution behavior typical for immediate-release formulations. The composition of the present invention exhibits a dissolution rate of less than 15% in 30 minutes when tested in 300 ml 0.03 N hydrochloric acid pH 1.2 and at least 75% in 90 minutes when tested in 900 ml phosphate buffer pH 6.8 in a USP apparatus II at 50 rpm (normal vessel) at 37° C.

The tablet composition in accordance with the present invention may be used as a medicament. The composition typically may be used in the treatment of castration-resistant prostate cancer.

The following examples are intended to illustrate the scope of the present invention but not to limit it thereto.

EXAMPLES

Example 1

Pharmaceutical Composition Comprising a Co-Precipitate of Enzalutamide and HPMCAS (1:5)

The film-coated tablets comprising a co-precipitate of enzalutamide and HPMCAS have the composition as given in table 1.

TABLE 1

| | Tablet composition | |
|---|---|---|
| Component | mg/tablet | % |
| Intragranular components | | |
| Enzalutamide | 80.00 | 12.31 |
| HPMCAS | 400.00 | 61.54 |
| Mannitol | 108.25 | 16.65 |
| Croscarmellose sodium | 26.00 | 4.00 |
| Acetone | 2720 | q.s. |
| Extragranular components | | |
| Croscarmellose sodium | 26.00 | 4.00 |
| Colloidal silicon dioxide | 3.25 | 0.50 |
| Magnesium stearate | 6.50 | 1.00 |
| Total core tablet weight | 650.00 | 100.00 |
| Opadry Yellow | 19.50 | 3.00 |
| Total coated tablet weight | 669.50 | 103.00 |

The tablets were prepared by the process as depicted in the flowchart of FIG. 1, without the optional steps of adding surfactant and dry granulation.

XRPD analysis performed after storage of the film coated tablets for 6 months at 40° C./75% RH in Alu, Triplex 120 and Triplex 180 blisters showed that no conversion into any crystalline form of enzalutamide was observed.

The tablets obtained, exhibited a dissolution rate of less than 15% in 30 minutes when tested in 300 ml 0.03 N hydrochloric acid pH 1.2 and at least 75% in 90 minutes when tested in 900 ml phosphate buffer pH 6.8 in a USP apparatus II at 50 rpm (normal vessel) at 37° C.

Example 2

Pharmaceutical Composition Comprising a Co-Precipitate of Enzalutamide, HPMCAS (1:5) and Poloxamer The film-coated tablets comprising a co-precipitate of enzalutamide, HPMCAS and poloxamer have the composition as given in table 2.

TABLE 2

| | Tablet composition | |
|---|---|---|
| Component | mg/tablet | % |
| Intragranular components | | |
| Enzalutamide | 80.00 | 12.31 |
| HPMCAS | 400.00 | 61.54 |
| Poloxamer 188 | 9.75 | 1.50 |
| Microcrystalline cellulose | 98.50 | 15.15 |
| Croscarmellose sodium | 26.00 | 4.00 |
| Acetone | 2720.00 | q.s. |
| Water | 87.75 | q.s. |
| Extragranular components | | |
| Croscarmellose sodium | 26.00 | 4.00 |
| Colloidal silicon dioxide | 3.25 | 0.50 |
| Magnesium stearate | 6.50 | 1.00 |
| Total core tablet weight | 650.00 | 100.00 |
| Opadry Yellow | 19.50 | 3.00 |
| Total coated tablet weight | 669.50 | 103.00 |

The tablets were prepared by the process as depicted in the flowchart of FIG. 1, without the optional step of dry granulation.

XRPD analysis performed after storage of the film coated tablets for 3 months at 40° C./75% RH in Alu and Triplex 120 blisters showed that no conversion into any crystalline form of enzalutamide was observed.

The tablets obtained, exhibited a dissolution rate of less than 15% in 30 minutes when tested in 300 ml 0.03 N hydrochloric acid pH 1.2 and at least 75% in 90 minutes when tested in 900 ml phosphate buffer pH 6.8 in a USP apparatus II at 50 rpm (normal vessel) at 37° C.

Example 3

Pharmaceutical Composition Comprising a Co-Precipitate of Enzalutamide and HPMCP (1:5)

The film-coated tablets comprising a co-precipitate of enzalutamide and HPMCP have the composition as given in table 3.

TABLE 3

| | Tablet composition | |
|---|---|---|
| Component | mg/tablet | % |
| Intragranular components | | |
| Enzalutamide | 80.00 | 12.31 |
| HPMCP | 400.00 | 61.54 |
| Microcrystalline cellulose | 108.25 | 16.65 |
| Croscarmellose sodium | 26.00 | 4.00 |
| Acetone | 2467.08 | q.s. |
| Water | 129.85 | q.s. |
| Extragranular components | | |

TABLE 3-continued

| Component | Tablet composition mg/tablet | % |
|---|---|---|
| Croscarmellose sodium | 26.00 | 4.00 |
| Colloidal silicon dioxide | 3.25 | 0.50 |
| Magnesium stearate | 6.50 | 1.00 |
| Total core tablet weight | 650.00 | 100.00 |
| Opadry Yellow | 19.50 | 3.00 |
| Total coated tablet weight | 669.50 | 103.00 |

The tablets were prepared by the process as depicted in the flowchart of FIG. 1, without the optional steps of adding surfactant and dry granulation.

XRPD analysis performed after storage of the film coated tablets for 1 month at 40° C./75% RH in Alu and Triplex 180 blisters showed that no conversion into any crystalline form of enzalutamide was observed.

The tablets obtained, exhibited a dissolution rate of less than 15% in 30 minutes when tested in 300 ml 0.03 N hydrochloric acid pH 1.2 and at least 75% in 90 minutes when tested in 900 ml phosphate buffer pH 6.8 in a USP apparatus II at 50 rpm (normal vessel) at 37° C.

Example 4

Pharmaceutical Composition Comprising a Co-Precipitate of Enzalutamide and HPMCP (1:4)

The film-coated tablets comprising a co-precipitate of enzalutamide and HPMCP have the composition as given in table 4.

TABLE 4

| Component | Tablet composition mg/tablet | % |
|---|---|---|
| Intragranular components | | |
| Enzalutamide | 80.00 | 12.31 |
| HPMCP | 320.00 | 49.23 |
| Microcrystalline cellulose | 188.25 | 28.96 |
| Croscarmellose sodium | 26.00 | 4.00 |
| Acetone | 1958.46 | q.s. |
| Water | 103.08 | q.s. |
| Extragranular components | | |
| Croscarmellose sodium | 26.00 | 4.00 |
| Colloidal silicon dioxide | 3.25 | 0.50 |
| Magnesium stearate | 6.50 | 1.00 |
| Total core tablet weight | 650.00 | 100.00 |
| Opadry Yellow | 19.50 | 3.00 |
| Total coated tablet weight | 669.50 | 103.00 |

The tablets were prepared by the process as depicted in the flowchart of FIG. 1, without the optional steps of adding surfactant and dry granulation.

XRPD analysis performed after storage of the film coated tablets for 1 month at 40° C./75% RH in Alu and Triplex 180 blisters showed that no conversion into any crystalline form of enzalutamide was observed.

The tablets obtained, exhibited a dissolution rate of less than 15% in 30 minutes when tested in 300 ml 0.03 N hydrochloric acid pH 1.2 and at least 75% in 90 minutes when tested in 900 ml phosphate buffer pH 6.8 in a USP apparatus II at 50 rpm (normal vessel) at 37° C.

The invention claimed is:

1. A tablet composition comprising a granulate consisting of a co-precipitate on a substrate, wherein the co-precipitate comprises enzalutamide in amorphous form and a cellulosic concentration enhancing polymer;

wherein said granulate was obtained by spraying a solution comprising the enzalutamide and the cellulosic concentration enhancing polymer over the substrate and subsequently drying to obtain said co-precipitate on the substrate;

wherein said cellulosic concentration enhancing polymer is selected from hydroxylpropylmethylcellulose acetate succinate (HPMCAS) and hydroxypropylmethylcellulose phthalate (HPMCP);

wherein the substrate comprises a sugar alcohol, microcrystalline cellulose, or mixtures thereof.

2. The tablet composition according to claim 1, wherein a weight ratio of enzalutamide to the cellulosic concentration enhancing polymer ranges from 1:2 to 1:6.

3. The tablet composition according to claim 1, wherein the sugar alcohol is mannitol.

4. The tablet composition according to claim 1, wherein the substrate further comprises a disintegrant.

5. The tablet composition according to claim 4, wherein the disintegrant is croscarmellose sodium.

6. The tablet composition according to claim 1, wherein the co-precipitate further comprises a surfactant.

7. The tablet composition according to claim 6, wherein the surfactant is a poloxamer.

8. The tablet composition according to claim 1, further comprising pharmaceutically acceptable excipients.

9. The tablet composition according to claim 8, wherein the pharmaceutically acceptable excipients are selected from one or more diluents, disintegrants, glidants or lubricants.

10. The tablet composition according to claim 1, wherein the composition exhibits a dissolution rate of less than 15% in 30 minutes when tested in 300 ml 0.03 N hydrochloric acid pH 1.2 and at least 75% in 90 minutes when tested in 900 ml phosphate buffer pH 6.8 in a USP apparatus II at 50 rpm (normal vessel), 37° C.

11. A process to prepare the tablet composition according to claim 1, comprising the following steps:

a) dissolving enzalutamide, the cellulosic concentration enhancing polymer and optionally a surfactant in a solvent system comprising acetone to form the solution;

b) spraying the solution over the substrate;

c) drying the obtained granulate;

d) blending with further pharmaceutically acceptable excipients;

e) compressing into tablets;

f) optionally coating of the tablets.

12. The process according to claim 11, wherein step b) is executed in a fluid bed granulator.

13. The process according to claim 11, further comprising the step of dry granulation after step c).

14. A method for treating castration-resistant prostate cancer, which comprises administering the tablet composition according to claim 1 to a patient that has castration-resistant prostate cancer.

15. The method according to claim 14, wherein said tablet contains 80 mg of said enzalutamide.

* * * * *